(12) United States Patent
Gurley et al.

(10) Patent No.: US 12,168,105 B2
(45) Date of Patent: *Dec. 17, 2024

(54) OCCLUSION ACCESS SYSTEMS

(71) Applicant: Merit Medical Systems, Inc., South Jordan, UT (US)

(72) Inventors: John Gurley, Lexington, KY (US); Joseph Creagan Trautman, Sunnyvale, CA (US); Brice Arnault De La Menardiere, Santa Cruz, CA (US); Clayton Baldwin, Santa Cruz, CA (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/480,388

(22) Filed: Oct. 3, 2023

(65) Prior Publication Data
US 2024/0139473 A1    May 2, 2024

Related U.S. Application Data

(63) Continuation of application No. 17/811,807, filed on Jul. 11, 2022, now Pat. No. 11,806,485, which is a continuation of application No. 16/154,106, filed on Oct. 8, 2018, now Pat. No. 11,383,065, which is a
(Continued)

(51) Int. Cl.
| | | |
|---|---|---|
| *A61B 5/00* | (2006.01) | |
| *A61B 5/06* | (2006.01) | |
| *A61B 17/34* | (2006.01) | |
| *A61M 25/01* | (2006.01) | |
| *A61M 25/09* | (2006.01) | |
| *A61M 29/02* | (2006.01) | |
| *A61B 17/22* | (2006.01) | |
| *A61B 17/3207* | (2006.01) | |
| *A61B 90/00* | (2016.01) | |
| *A61M 25/00* | (2006.01) | |

(52) U.S. Cl.
CPC ......... *A61M 25/0108* (2013.01); *A61B 5/064* (2013.01); *A61B 17/3478* (2013.01); *A61M 25/0136* (2013.01); *A61M 25/09* (2013.01); *A61M 29/02* (2013.01); *A61B 2017/22094* (2013.01); *A61B 2017/22095* (2013.01); *A61B 17/3207* (2013.01); *A61B 2090/3966* (2016.02); *A61M 2025/0008* (2013.01); *A61M 2025/0089* (2013.01); *A61M 2025/0166* (2013.01); *A61M 2029/025* (2013.01); *A61M 2205/0266* (2013.01)

(58) Field of Classification Search
CPC .............................. A61B 5/064; A61M 25/108
See application file for complete search history.

(56) References Cited

U.S. PATENT DOCUMENTS

| | | |
|---|---|---|
| 9,289,577 B2 | 3/2016 | Gurley et al. |
| 10,092,726 B2 | 10/2018 | Gurley et al. |
| 11,383,065 B2 | 7/2022 | Gurley et al. |

(Continued)

OTHER PUBLICATIONS

Notice of Allowance dated Jul. 27, 2023 for U.S. Appl. No. 17/811,807.
Office Action dated Apr. 21, 2023 for U.S. Appl. No. 17/811,807.

*Primary Examiner* — Rajeev P Siripurapu
(74) *Attorney, Agent, or Firm* — Dorsey & Whitney LLP

(57) ABSTRACT

A catheter system for accessing the central venous system through an occlusion in the neck region.

19 Claims, 7 Drawing Sheets

Related U.S. Application Data continuation of application No. 13/680,327, filed on Nov. 19, 2012, now Pat. No. 10,092,726.

(60) Provisional application No. 61/596,834, filed on Feb. 9, 2012.

(56) References Cited

U.S. PATENT DOCUMENTS

| | | | |
|---|---|---|---|
| 11,806,485 B2 * | 11/2023 | Gurley | A61B 17/3478 |
| 2012/0136320 A1 * | 5/2012 | Pillai | A61B 17/3403 604/272 |
| 2023/0173230 A1 | 6/2023 | Gurley et al. | |

* cited by examiner

OCCLUSION ACCESS SYSTEMS

CROSS REFERENCE TO RELATED CASES

This application is a continuation of U.S. patent application Ser. No. 17/811,807 filed Jul. 11, 2022, titled 'OCCLUSION ACCESS METHOD', which is a continuation of U.S. patent application Ser. No. 16/154,106 filed Oct. 8, 2018, titled 'OCCLUSION ACCESS METHOD', issued as U.S. Pat. No. 11,383,065 on Jul. 12, 2022, which is a continuation of U.S. patent application Ser. No. 13/680,327 filed Nov. 19, 2012, titled 'OCCLUSION ACCESS SYSTEM', issued as U.S. Pat. No. 10,092,726 on Oct. 9, 2018, which claims priority to U.S. Provisional Application No. 61/596,834 filed Feb. 9, 2012. The entire contents of each of the above-referenced applications is specifically incorporated by reference herein without disclaimer.

BACKGROUND OF THE INVENTION

Access to the central venous system of a patient is necessary to carry out many life-saving medical procedures. The usual method of gaining access to the venous system in the area of the neck is to directly puncture a major vein in the neck with a large gauge needle through which a guide wire is placed. The guide wire supports the remainder of the intervention at the site that usually results in the placement of an introducer sheath or the like. A problem arises when a major vein is blocked with a clot or fibrous occlusion. In this instance the usual standard of care is to acquire venous access via another or alternate major vessel in the neck region. The sequential sacrifice of major vessels is quite common but it is believed by the inventors to be a very undesirable practice.

Prior art references of note include Pillai publications (US 2012/0136320) and (US 2012/0136247) which together teach the use of a soft pliant dual lumen catheter to achieve central venous access in an alternative fashion to the conventional direct puncture technique. Pillai does not propose a solution to the recovery or salvage of an already occluded vessel. In Pillai the user introduces a dual lumen sheath in to the venous vascular system in the groin or arm and navigates the pliant sheath or catheter to the internal jugular vein, for example.

Next a stiff shaped wire is placed in to one of the lumens and it forces the soft pliant tip into a hook shape. Next a sharp needle wire is forced through the now curved companion lumen and it pierces the vessel and is pushed out of the body.

Evans (US 2004/0181150), by way of contrast, teaches the use of a soft pliant catheter. This catheter is used to enter into a body lumen, subsequently a hollow or open lumen shaped tube is advanced out of the catheter. The curved tube and a companion wire located within the lumen are pushed together through the wall of the body lumen and to exteriorize the assembly from the patient's body along an arcing and therefore not linear path.

Applicant believes that these approaches are unusable in the presence of an occlusion as neither reference teaches the use of their devices in an occlusion.

These two concepts are unlike the present invention. Applicant's device can in fact enter an occluded vessel and reliably aim and launch a needle wire along a straight pre-determined trajectory to a desired and pre-determined exit location indicated and defined on the surface of the patient with a radiopaque external target marker.

SUMMARY OF THE INVENTION

The present invention relates to a catheter system used to gain access to a patient's central venous system through an occluded large vessel in the neck at a location near the clavicle. In contrast to conventional practice the central venous system is approached from the inside out, with the initial entry point in the groin area and an exit location near and usually above the clavicle.

In use, a radiopaque target is placed on the surface of the patient to identify and mark the desired and pre-determined exit point for a so-called needle wire.

Typically, an elongate working catheter is introduced into the venous system though the femoral vein in the groin using a conventional cut down technique. Usually a delivery sheath will be introduced over a guide wire and navigated to the approximate location of the stump of the occlusion and then the working catheter portion of the inventive system is delivered to that site through the delivery sheath after the removal of the guide wire.

It is important to note that the working section of the elongate working catheter emerges from the delivery sheath and this working section has sufficient stiffness to be pushed, torqued and translated with enough force to permit a distal blunt dissection tip terminating the working section to be forced into the occlusion in the vessel.

The radiopaque marker device or target on the exterior surface of the patient defines a desired exit location reference point and the marker is used fluoroscopically to assist in guiding the working section of the elongate catheter into position. The working section is manipulated, oriented and aimed by translating and rotating the working section, while visualizing it fluoroscopically with respect to an aperture in the surface target. A structural feature near the tip allows for the setting of a departure angle plane that places the needle wire guide 10 in a plane that intersects the exit point on the surface of the patient. In one embodiment a departure angle is read from the fluoroscopic visualization equipment (C-arm X-ray) and this departure angle is entered or set on a companion catheter handle. The departure angle setting causes a needle wire departure angle guide tube to emerge from a side hole in the appropriate plane 15 and near to aim the needle wire at the departure angle that ensures that the needle wire is aimed directly toward the exit target aperture. In an alternate embodiment the departure angle is fixed in the catheter and the C-arm is set to the departure angle and the catheter working section is positioned to align with the target.

Once aimed by these structures and this process, a needle wire is advanced. The needle wire is pushed through the departure angle guide tube to traverse the occlusion, transect the vessel wall and form a straight tissue track toward the surface target where it is exteriorized. With the needle wire exteriorized through the central aperture of the exit target it is preferred to remove the working section and elongate working catheter from the body and use the needle wire to pull a dilation catheter along the tissue tack thus enlarging it. This dilation may be easily achieved by dragging a dilation catheter from the exit wound near the clavicle into the central venous system through the occlusion by pulling on the needle wire from the femoral location. In one embodiment the needle wire may be locked to the handle and the removal of the working catheter draws the needle wire ante-grade. Once enlarged by dilation the tissue track is ready for conventional use, which may be supported by the introduction an introducer or the like in the ante grade direction.

BRIEF DESCRIPTION OF THE DRAWINGS

Throughout the several FIGURES identical reference numerals indicate identical structures wherein.

DETAILED DESCRIPTION OF THE INVENTION

Figure 1:
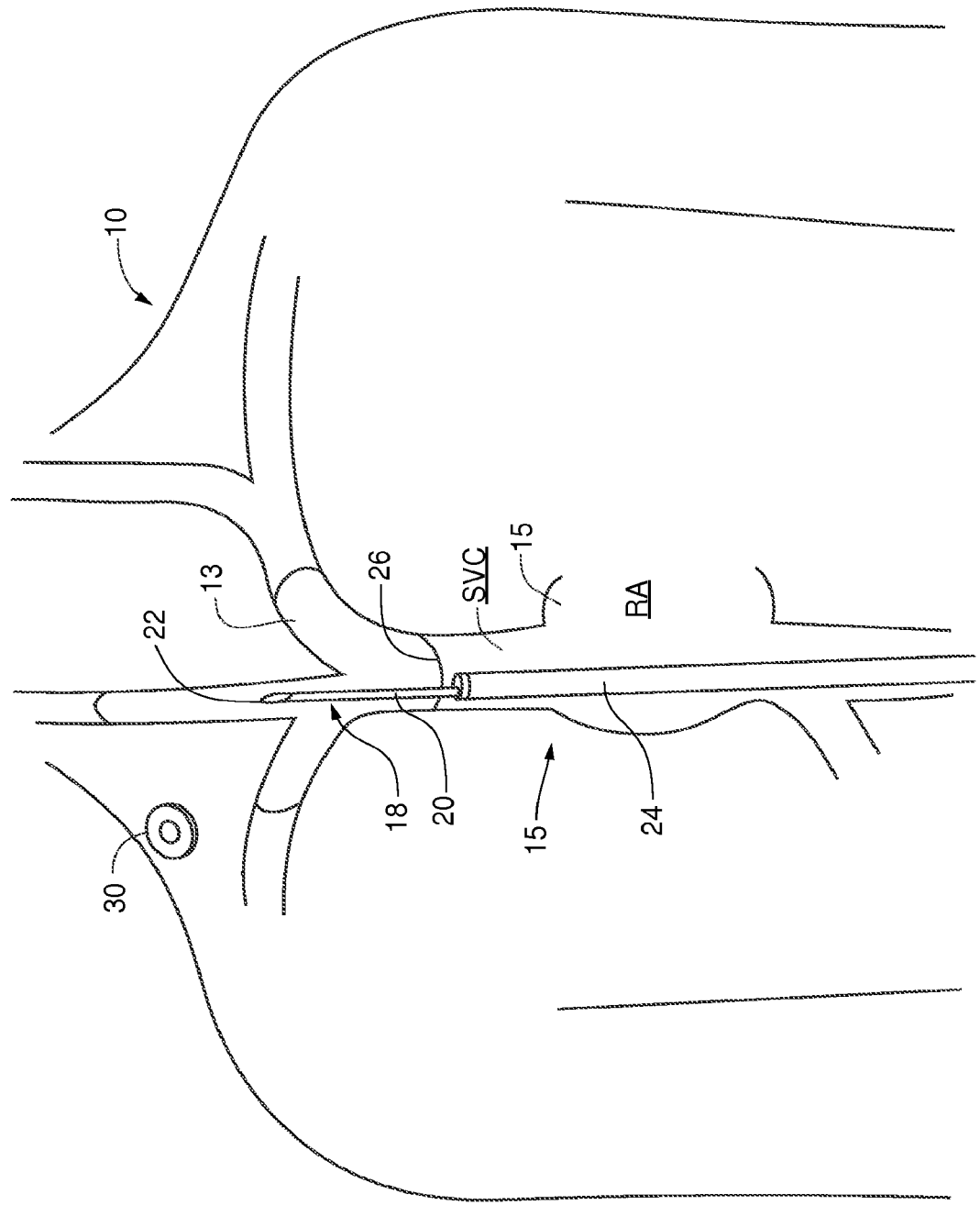
FIG. 1 is a schematic drawing of a patient showing the context of the invention.

FIG. 1 shows a patient 10 with a complex occlusion 13 involving several vessels in neck region above the level of the superior vena cava and the right atrium near reference numeral 15. In the figure, the working section 18 of the elongate working catheter 20 has entered the occlusion 13 via blunt dissection.

The blunt dissection distal tip 22 of the working section 18 is being pushed in to the occlusion by forces applied to a handle (not seen in this view) attached to the proximal end of the elongate working catheter 20. The user is advancing the blunt dissection tip toward the patient's head. This motion will place the blunt tip 22 in the vicinity of the radiopaque marker 30 on the surface of the patient.

Also seen in this view is a delivery sheath 24 of conventional design used to help position the elongate working catheter 20 at the stump 26 of the occlusion.

Figure 2:
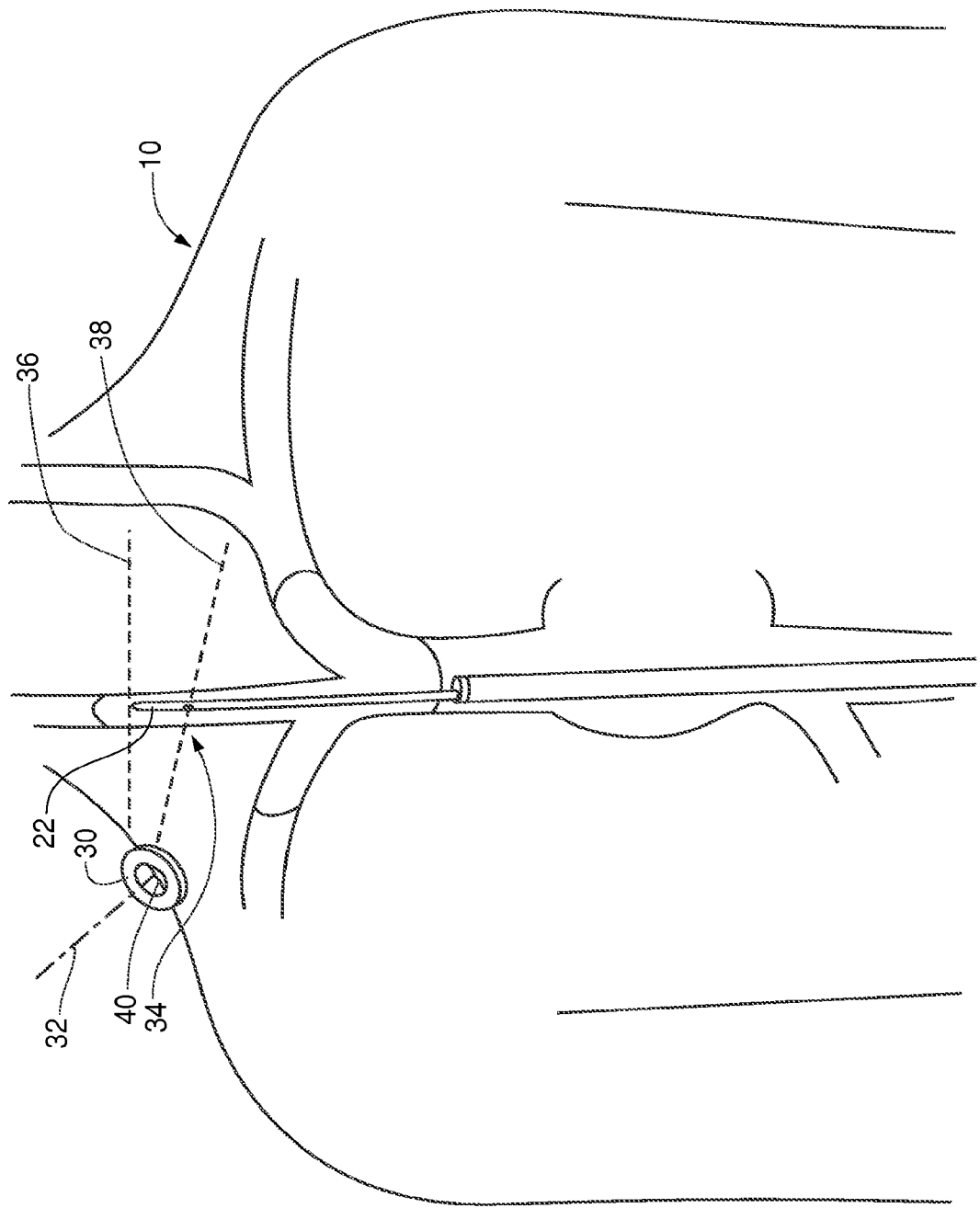
FIG. 2 is a schematic drawing of a patient showing the invention with the needle wire advanced.

FIG. 2 shows that the radiopaque target 30 placed on the surface of the patient serves to define a desired exit point 40 on the surface of the patient. As described in more detail below, the closed end blunt dissection tip 22 is imaged via fluoroscopy (anterior/posterior) and the tip 22 is moved to a desired distal end location 36. Once the desired tip location is achieved, the C-arm cranial angle is observed and it is used to set the departure angle. In general, the C-arm is moved to image the tip 22 through the target 30. The angular location of the blunt tip is determined by a slot feature in the blunt dissection tip; this feature is seen better in detail FIG. 5. As the blunt tip is rotated around its long axis the opacity of the slot varies and this changing image feature is used to determine the orientation of the exit plane of the departure angle guide. Once the appropriate tip position 36 has been achieved, the C-arm is moved to image the tip 22 through the target 30. The C-arm cranial angle is observed and it is used to set the departure angle that defines a tissue track 38 angle that aims the sharp dissection tip of the needle wire 32 toward the central aperture of the radiopaque target 30 via forces supplied by the user to the needle wire 32 through a handle not seen in this view. With the needle wire 32 exteriorized as seen in the figure the access provided to the end of the wire allows additional intervention at the exit wound site as described below.

Figure 3:
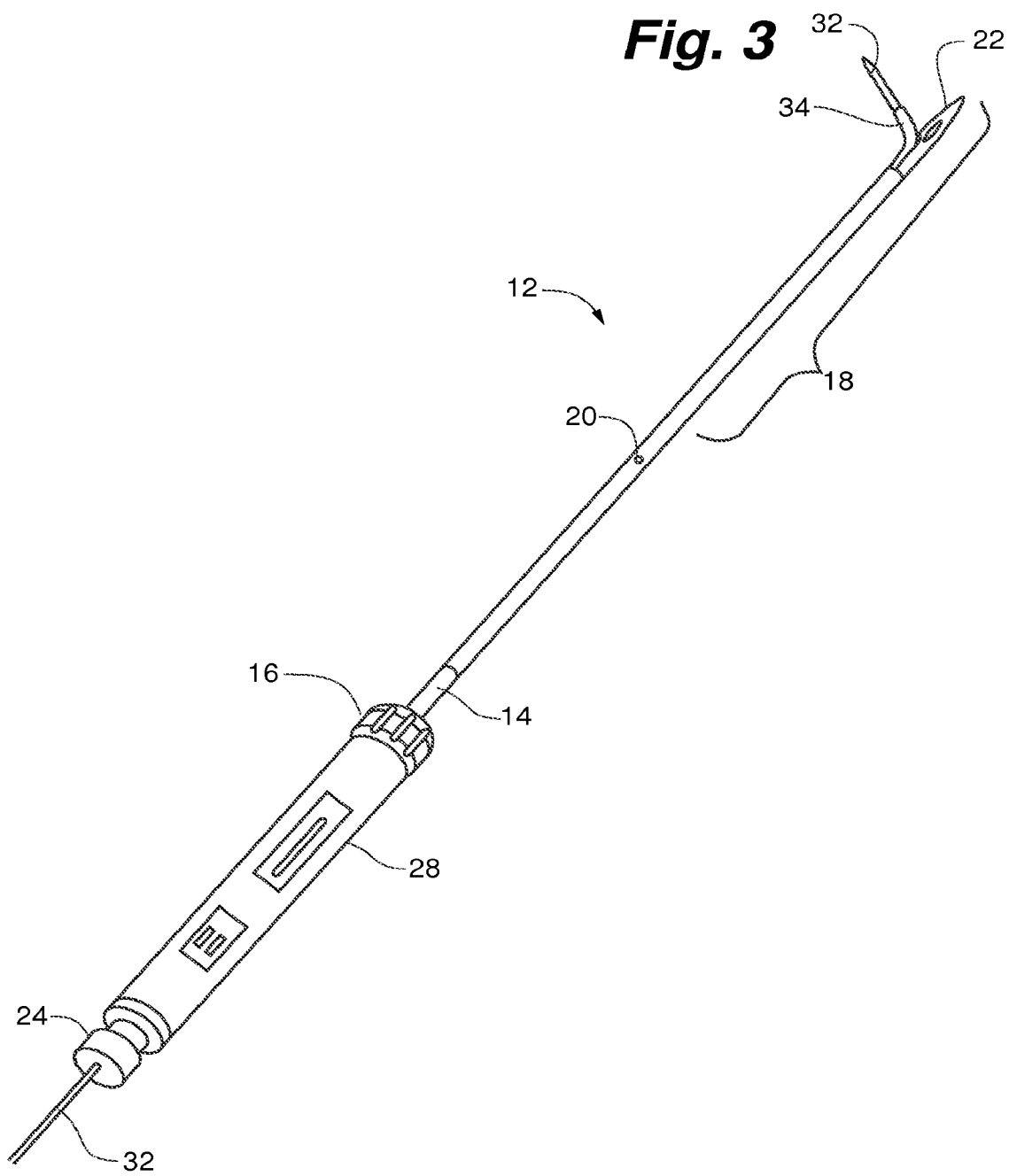
FIG. 3 is a perspective drawing of the working catheter of the invention.

FIG. 3 shows the catheter system 12 in isolation. The shaft of the working catheter 20 is connected to a handle 28 through a strain relief 14. The distal working section of the catheter 18 and the shaft of the working catheter 20 are sufficiently push-able and torque-able to allow the blunt dissection tip 22 to be forced into the occlusion. Experimentation has established that an appropriate value of bending stiffness is around 52 (pounds force) times (inches squared). A stainless steel tube with an inside diameter of 0.074 inches and outside diameter of 0.094 inches is sufficient for this purpose and meets this parameter. However it is anticipated that variable wall thickness structures and otherwise flexible materials can be readily substituted. For example, braided nitinol embedding in a polymer or a laser cut hypodermic tube may be used. The functional characteristic required is sufficient push-ability and torque-ability to permit entry into the occlusion via blunt dissection. Of course, the magnitude of the forces required also depend on the "sharpness" of the blunt dissection tip 22 feature and the overall diameter of the blunt tip itself. In general, the tip is blunt enough that it will not penetrate skin if it is touched while handling the catheter.

Figure 4:
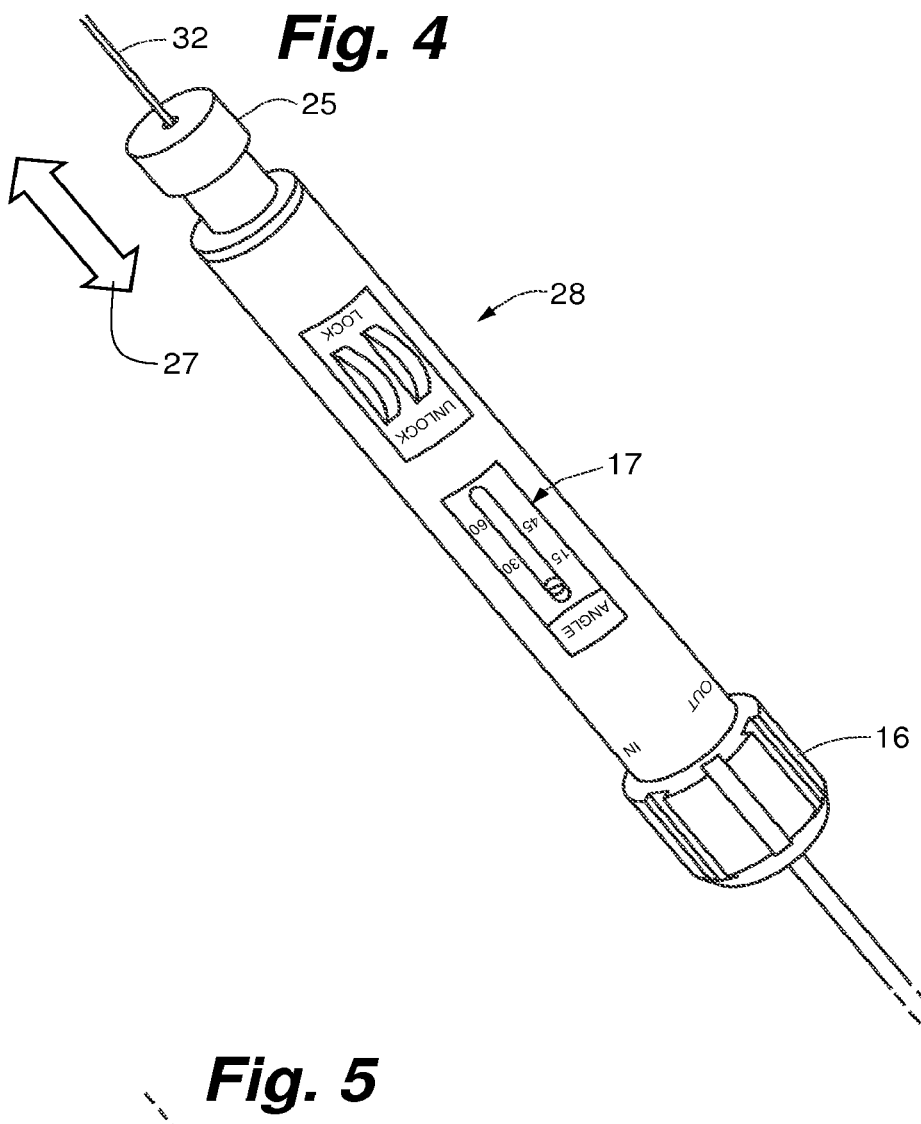
FIG. 4 is a perspective drawing of a portion of the working catheter of the invention.
Figure 5:
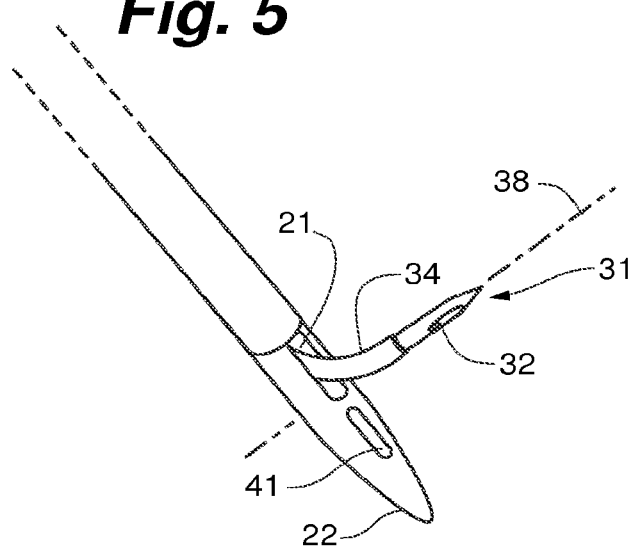
FIG. 5 is a perspective drawing of a portion of the working catheter of the invention.

FIG. 4 and FIG. 5 should be considered together, where FIG. 4 shows details of the handle 28 and FIG. 5 shows details of the tip. In use, the rotary knob 16 may be turned or twisted (FIG. 4) to advance the needle wire departure angle guide tube out of the blunt dissection tip 22 side aperture 21 (FIG. 5). The position of the needle wire departure angle guide tube 34 and the departure angle is read from a gauge 17 in the handle 28. Thus the knob sets the departure angle which is read from the gauge on the handle. The plane of the departure angle guide is set by the rotation of the handle 28 itself and visualization of the opacity of the aperture feature 21 in the distal tip.

In use, a wire clamping and propelling system located within the handle 28 allows the user to advance the needle wire 32 out of the handle with a "pumping motion", as indicated by motion arrow 27. This may be achieved in this embodiment by reciprocating the sliding pommel 25 to advance the needle wire 32 through the handle and out of the needle wire departure angle guide tube 34 along path 38 defined by the rotational plane of the needle wire departure angle guide tube and the location 26 (FIG. 1) of the blunt dissection distal tip 22 relative to the target 30 (FIG. 1 and FIG. 2).

Figure 6:
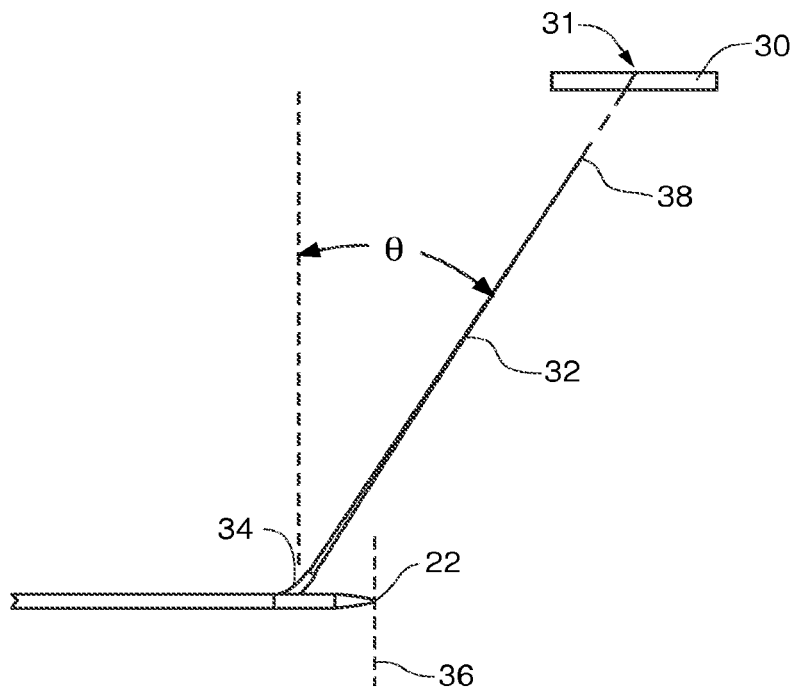
FIG. 6 is a schematic drawing of a portion of the working catheter of the invention showing a lateral view of the aiming process.
Figure 7:
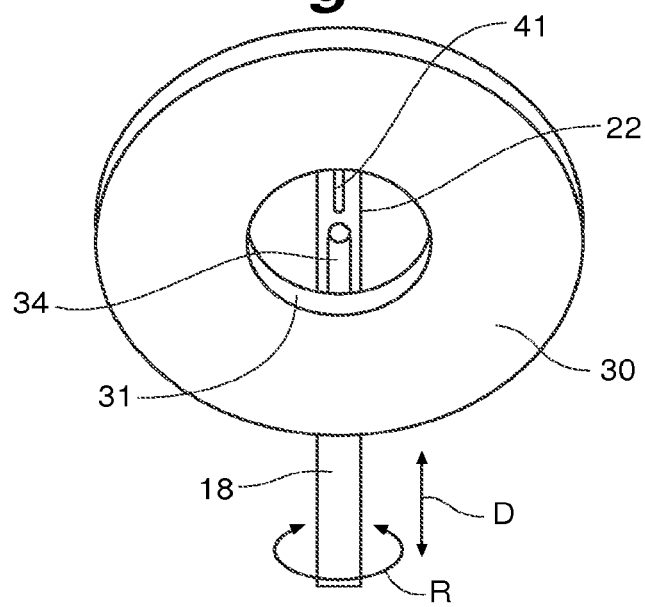
FIG. 7 is a perspective drawing of a portion of the working catheter of the invention seen through with the exit target.
Figure 10:
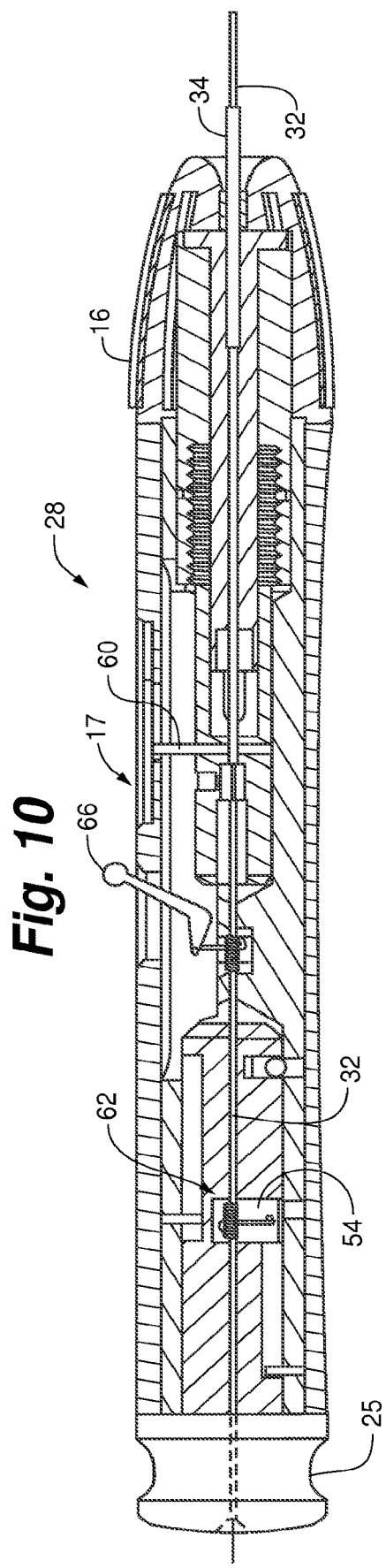

FIG. 6 and FIG. 7 should be considered together. Together they illustrate the use of the radiopaque marker 30 positioned on the surface of the patient to facilitate catheter setup and aiming. The goal is to quickly, via C-arm fluoroscopy, determine the optimal distal tip location or position 36 as well as the optimal departure angle (theta in the figure) that correspond to the alignment of the needle wire 32 with the central aperture 31 of target 30. With the proper selection of the distal tip position 36 and departure angle theta, the tissue track 38 traversed by the needle wire 32 will track in a straight line and exit the body at the desired and pre-defined location. FIG. 6 shows the relationship between tip location 36 and the appropriate departure angle theta. In the figure, the anatomic structures are not shown to simplify and clarify the figure. In general, these two variables are complimentary and various values can be selected to ensure that the tissue track 38 does not transect the clavicle. FIG. 7 is a schematic and simplified and highly stylized view of the image the user would see via C-Arm fluoroscopy. The blunt dissection tip 22 has a slot aperture 41 that can be viewed through the central aperture 31 of radiopaque target 30. The opacity of the slot 41 will vary with the rotation indicated by motion arrow "R" of the working section of the catheter. In general the slot will appear brightest when the plane of the needle wire guide tube is "aimed" at the central aperture 31; that is, the plane of the guide tube intersects the exit point on the patient. This will be true when the viewing axis of the fluoroscope (VAF) is aligned with the target which is assumed to be the case in this description. The user will advance or retract the tip 22 ("D") and rotate ("R") the working section 18 to optimize the location of the planned tissue track 38. Once alignment has been selected, an angle corresponding to theta is read off the C-Arm and used to set the guide tube position or departure angle. In the embodiment of FIG. 4 and FIG. 10 the knob 16 is twisted until the scale 17 corresponds to the desired departure angle. The angular range varies from about 15 degrees to 60 degrees as indicated on the handle. This corresponds to the operational angle seen on FIG. 6 of about 75 degrees to 30 degrees as measured perpendicular to the axis of the shaft.

Figure 8:
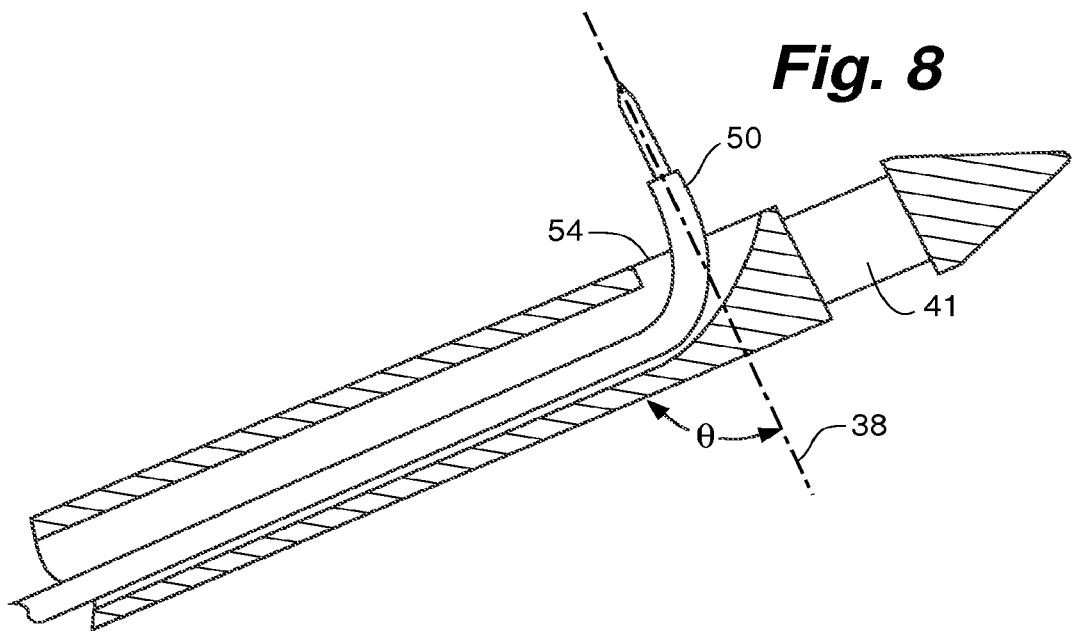
FIG. 8 is a schematic drawing of an alternate embodiment of the distal tip region of a working section with a guide tube advanced outside the working section.
Figure 9:
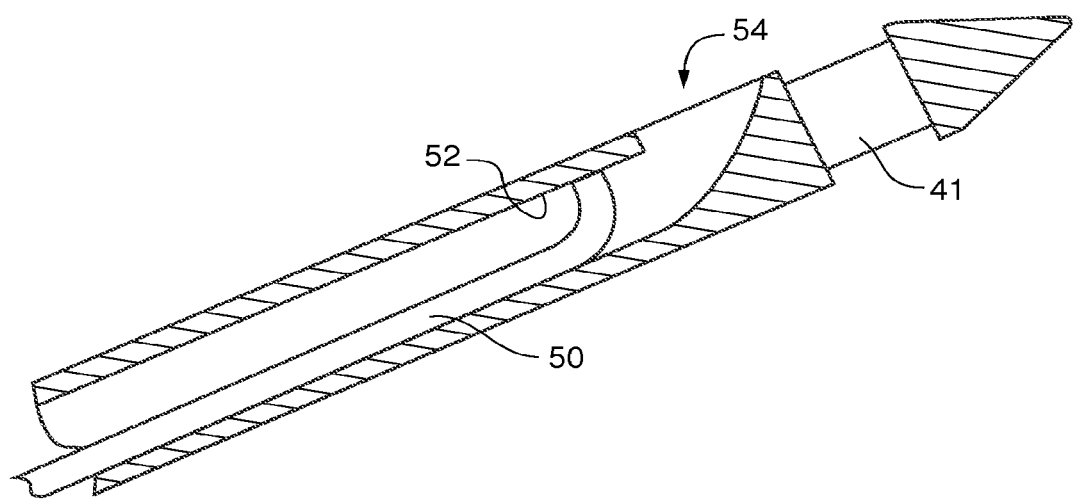
FIG. 9 is schematic drawing of an alternate embodiment of the distal tip region of a working section with a guide tube retracted within the working section; and, FIG. 10 is a cross section of an embodiment of the proximal handle portion of the working catheter.

FIG. 8 and FIG. 9 should be considered together. They represent an alternative embodiment of the system where the needle wire departure angle guide tube 50 has a fixed value that is not adjustable by the user. The fixed departure angle device differed from the variable angle device in that a degree of freedom is eliminated. That is, the linear travel of the needle guide with respect to the tip have only one correct value to achieve target aiming. Only the distal section of the device is shown and the remaining details of handle construction are well known to those of skill in the art and need not be further described. The super-elastic departure angle guide tube 50 has a value of approximately 90 degrees in FIG. 8. As the needle wire departure angle guide tube is advanced distally within lumen 52 it emerges through a port 54 and assumes it preset configuration defining tissue track 38. The advantage of this construction is simplicity but in general there will be only one distal tip location that will transect the target aperture. Once again the rotational angle of the plane of the departure angle is ascertained via C-arm fluoroscopy where the "brightness" of a feature which in this embodiment is a densely radiopaque marker 56 applied to the tip to facilitate aiming.

FIG. 10 is a cross section of the handle with an illustrative implementation of structures for carrying out the wire management and departure angle setting features. This embodiment is intended to be illustrative but not limiting. Some items described previously are absent from this view to simplify and clarify the operation of the handle. The handle is approximately cylindrical with a central axis. A portion of the needle wire departure guide tube is seen at 34. Rotation of the knob 16 turns a screw that advances or retracts the tube 34 depending upon direction of rotation. The position of the tube and therefore the departure angle is indicated by the position of post 60 in its companion slot. The user twists the knob 16 until the indicator post indicates the desired departure angle as read from the gauge or scale 17 seen best in FIG. 4. The pommel 25 interacts with a J-arm clamp 62 that is pivoted 64 to wedge against the wire 32 as the pommel is advanced distally in the handle. The return stroke allows the J-arm clamp to release the wire which will remain stationary while the pommel is moved again to its start position in preparation for another stroke of wire advancement. The pommel and handle structures together support the wire 32 during the stroke so that the wire does not bend or kink. The stroke is relatively fixed so that a user may count the number of pommel strokes to have an estimate of how much wire has been advanced out the guide tube.

An optional locking and releasing structure 66 can be used to connect the wire to the handle so the withdrawal of the handle also pulls the wire 32 or alternatively the wire 32 may be released entirely from the handle to allow the wire 32 to remain in the body while the handle and associated structures are removed from the body over the wire.

What is claimed is:

1. A catheter system for use by a user for gaining access to the central venous system of a patient through an occlusion in a large vessel in the upper chest region of said patient, the catheter system comprising:
   a radiopaque target having a radiopaque area and a radiolucent area configured to be applied to the exterior of said patient and define an exit point;
   an elongate working catheter having a proximal end and a distal end including a side aperture;
   a handle coupled to said proximal end of said elongate working catheter;
   a departure angle guide tube configured to be disposed distally within the elongate working catheter and adapted to emerge from the side aperture thereby defining a needle wire exit plane;
   a needle wire contained and located within said departure angle guide tube and adapted for relative motion with respect to said departure angle guide tube and extension through the departure angle guide tube at a departure angle in the departure angle plane, said needle wire having a sharp dissection tip configured to be forced through the occlusion, the vessel wall intervening tissue and skin to exteriorize at the surface of the patient at said exit point.

2. The catheter system of claim 1, further comprising a blunt dissection tip at the distal end of the elongate working catheter, wherein said blunt dissection tip includes:
   the side aperture; and
   a radiopaque feature that varies in contrast under x-ray as a function of the angle of rotation of the blunt dissection tip, thereby allowing the user to aim and orient the exit plane under fluoroscopic guidance.

3. The catheter system of claim 2, wherein said radiopaque feature is an aperture formed within a body of said blunt dissection tip.

4. The catheter system of claim 1, further including:
   a knob located on said handle adapted for rotation with respect to said handle; and
   a screw attached to said departure angle guide tube such that rotation of the knob controls the advancement and retraction of said departure angle guide tube.

5. The catheter system of claim 4 further including:
   a scale for reading the relative position of said departure angle guide tube with respect to said distal end of the elongate working catheter.

6. The catheter system of claim 2, wherein the elongate working catheter has a stiffness configured push the blunt dissection to enter into an occlusion via forces applied by a user to the handle, and wherein the blunt dissection tip rotates responsive to rotation of the handle.

7. The catheter system of claim 1, wherein the departure angle guide tube includes a shape memory section formed as a curve.

8. The catheter system of claim 1, wherein the distal end of the elongate working catheter and the radiopaque target are configured to be visualized together to permit a determination of the departure angle, the needle wire exit plane, and a distal end location of the distal end of the elongate working catheter.

9. A catheter system, comprising:
- a radiopaque target having a radiopaque area and a radiolucent area, the radiopaque target configured to be applied to the exterior of a patient to define an exit point;
- a working catheter having a distal end and a proximal end;
- a handle coupled to the proximal end of the working catheter;
- a blunt dissection tip coupled to the distal end of the working catheter;
- a needle wire guide tube located in the working catheter and configured to extend from the blunt dissection tip at a departure angle; and
- a needle wire located in the needle wire guide tube and configured to be advanced out of the needle wire guide tube.

10. The catheter system of claim 9, wherein:
the blunt dissection tip includes a side aperture configured to receive the needle wire guide tube; and
the blunt dissection tip includes a slot.

11. The catheter system of claim 10, wherein the blunt dissection tip and the slot rotate responsive to rotation of the handle effective to define both a rotation position of the blunt dissection tip and an operating plane of the needle wire guide tube.

12. The catheter system of claim 11, wherein the handle is configured to be actuated and wherein the needle wire guide tube extends out of the blunt dissection tip responsive to actuation of the handle, thereby defining and selecting a departure angle for the needle wire in the operating plane.

13. The catheter system of claim 11, wherein:
the needle wire includes a sharp dissection tip;
the needle wire is configured to extend through the needle wire guide tube; and
the needle wire is configured to extend and track in a substantially straight line, lying substantially in the operating plane from the needle wire guide tube, thereby defining a straight tissue track.

14. The catheter system of claim 9, wherein:
the handle is configured to be actuated; and
the needle wire guide tube extends and advances responsive actuation of the handle.

15. The catheter system of claim 9, wherein: the handle is configured to be actuated;
the needle wire located in the needle wire guide tube advanced responsive to actuation of the handle.

16. The catheter system of claim 9, wherein the blunt dissection tip includes a side aperture and a radiopaque feature that varies in contrast under x-ray as a function of the angle of rotation of the blunt dissection tip.

17. The catheter system of claim 9, further comprising:
a knob located on the handle and rotatable relative to the handle; and
a screw attached to the needle wire guide tube and operated by the knob such that rotation of the knob controls the advancement and retraction of the needle wire guide tube.

18. The catheter system of claim 17, further comprising a scale on the handle for reading the relative position of the needle wire guide tube with respect to the distal end of the working catheter.

19. The catheter system of claim 9, wherein the needle wire guide tube includes a shape memory section formed as a curve.

* * * * *